(12) United States Patent
Wheatley et al.

(10) Patent No.: US 9,517,014 B2
(45) Date of Patent: Dec. 13, 2016

(54) OCT PROBE WITH PIVOTING FIBER

(71) Applicant: Novartis AG, Basel (CH)

(72) Inventors: Barry Lynn Wheatley, Oceanside, CA (US); Kambiz Parto, Laguna Hills, CA (US)

(73) Assignee: Novartis AG, Basel (CH)

( * ) Notice: Subject to any disclaimer, the term of this patent is extended or adjusted under 35 U.S.C. 154(b) by 58 days.

(21) Appl. No.: 14/267,548

(22) Filed: May 1, 2014

(65) Prior Publication Data

US 2015/0080718 A1 Mar. 19, 2015

Related U.S. Application Data

(60) Provisional application No. 61/878,311, filed on Sep. 16, 2013.

(51) Int. Cl.
| | |
|---|---|
| *A61B 5/00* | (2006.01) |
| *A61B 1/07* | (2006.01) |
| *A61B 1/00* | (2006.01) |
| *A61B 3/10* | (2006.01) |

(52) U.S. Cl.
CPC ............ *A61B 5/0084* (2013.01); *A61B 1/0016* (2013.01); *A61B 1/00172* (2013.01); *A61B 1/07* (2013.01); *A61B 3/102* (2013.01); *A61B 5/0066* (2013.01)

(58) Field of Classification Search
CPC ....... A61B 1/00172; A61B 1/07; A61B 3/102; A61B 5/0066; A61B 5/0084
See application file for complete search history.

(56) References Cited

U.S. PATENT DOCUMENTS

| | | | | |
|---|---|---|---|---|
| 5,905,829 | A | * | 5/1999 | Maenishi ............ G02B 6/2556 385/59 |
| 6,066,102 | A | | 5/2000 | Townsend et al. |
| 6,402,719 | B1 | | 6/2002 | Ponzi et al. |
| 6,485,413 | B1 | * | 11/2002 | Boppart ............. A61B 1/00096 356/450 |
| 6,564,087 | B1 | | 5/2003 | Pitris et al. |
| 7,616,986 | B2 | * | 11/2009 | Seibel ................ A61B 5/0062 250/227.26 |
| 2001/0023346 | A1 | | 9/2001 | Loeb |
| 2001/0055462 | A1 | * | 12/2001 | Seibel ............... A61B 1/00048 385/147 |
| 2002/0003915 | A1 | | 1/2002 | Sorin et al. |
| 2002/0111548 | A1 | | 8/2002 | Swanson et al. |

(Continued)

OTHER PUBLICATIONS

International Search Report and Written Opinion of the International Searching Authority, International Application No. PCT/US2014/040742 , Oct. 20, 2014, 9 pages.

(Continued)

*Primary Examiner* — Baisakhi Roy
(74) *Attorney, Agent, or Firm* — Darien Reddick (57) ABSTRACT

An OCT probe for imaging patient tissue may include an actuation system arranged to displace an optical fiber within a cannula. The actuation system may include a driver actuatable to displace a portion of the optical fiber, with the driver acting in an angled direction relative to the axis of the cannula. The actuation system also may include a pivot feature operably engaged with the optical fiber in a manner permitting the optical fiber to pivot on the pivot feature when the driver actuates to displace the portion of the optical fiber.

12 Claims, 5 Drawing Sheets

(56) References Cited

U.S. PATENT DOCUMENTS

| | | |
|---|---|---|
| 2004/0151441 A1 | 8/2004 | Bennett et al. |
| 2005/0004453 A1 | 1/2005 | Tearney et al. |
| 2005/0078910 A1* | 4/2005 | Hickingbotham ...... A61F 9/007 385/31 |
| 2006/0170930 A1 | 8/2006 | Li |
| 2006/0262379 A1 | 11/2006 | Choo et al. |
| 2007/0066983 A1 | 3/2007 | Maschke |
| 2007/0284516 A1 | 12/2007 | Bustamante et al. |
| 2008/0080206 A1* | 4/2008 | Charles .................. A61B 19/52 362/572 |
| 2008/0177183 A1 | 7/2008 | Courtney et al. |
| 2008/0243031 A1* | 10/2008 | Seibel .................. A61B 1/0008 600/566 |
| 2009/0028407 A1 | 1/2009 | Seibel et al. |
| 2009/0198125 A1 | 8/2009 | Nakabayashi et al. |
| 2009/0208143 A1 | 8/2009 | Yoon et al. |
| 2009/0268161 A1 | 10/2009 | Hart et al. |
| 2010/0228119 A1 | 9/2010 | Brennan et al. |
| 2012/0029354 A1 | 2/2012 | Mark et al. |
| 2012/0330101 A1 | 12/2012 | Brennan et al. |
| 2015/0080718 A1 | 3/2015 | Wheatley et al. |

OTHER PUBLICATIONS

International Search Report and Written Opinion for PCT/US2014/051092, Not yet published, 8 pages, dated Dec. 11, 2014.
European Search Report for Application No. 14843997.9, Publication No. EP3014319, Published May 4, 2016, 4 pages.
PCT International Preliminary Report on Patentability, PCT/US2014/040742, Mar. 22, 2016, 8 pages.

\* cited by examiner

OCT PROBE WITH PIVOTING FIBER

CROSS-REFERENCED TO RELATED APPLICATIONS

This application claims the benefit of U.S. Provisional Application No. 61/878,311, filed Sep. 16, 2013, the entire contents of which are incorporated herein by reference.

TECHNICAL FIELD

The present disclosure relates to apparatuses and methods for scanning tissue with an OCT probe, and more particularly, to apparatus and methods that have a pivoting optical fiber.

BACKGROUND

Optical Coherence Tomography (OCT) systems are used to capture and generate three-dimensional images of patient tissue layers. These systems include OCT probes that often invasively penetrate tissue to obtain visualization of tissue within a patient. In ophthalmology, OCT probes are used to obtain detailed images of tissue about the eye or even forming a part of the eye, such as the retina.

In use, an optical light beam is directed through the probe at the tissue. A small portion of this light reflects from sub-surface features of the tissue and is collected through the same probe. Most light is not reflected but, rather, diffusely scatters at large angles. In conventional imaging, this diffusely scattered light contributes to background that obscures an image. However, in OCT, a technique called interferometry records the optical path length of received photons, and provides data that rejects most photons that scatter multiple times before detection. This results in images that are more clear and that extend in the depth of the tissue.

SUMMARY

In an exemplary aspect, the present disclosure is directed to an OCT probe for imaging patient tissue. The OCT probe may include a cannula having a cannula axis. It may also have a selectively displaceable light-carrying optical fiber disposed within the cannula and having a distal end. The optical fiber may be arranged to emit light from the distal end. An actuation system may be arranged to displace the optical fiber within the cannula. The actuation system may include a driver actuatable to displace a portion of the optical fiber, the driver acting in an angled direction relative to the axis of the cannula. The actuation system also may include a pivot feature operably engaged with the optical fiber. The optical fiber may be pivotable about the pivot feature in response to a displacement of the portion of the optical fiber by the driver.

In an aspect, a stiffening tube may be disposed about the optical fiber and separating the optical fiber and the pivot feature. The stiffening tube may directly engage the pivot feature in a pivot relationship. In an aspect, the stiffening tube extends from at least the pivot feature to the driver. In an aspect, the OCT probe may include a constraining feature disposed in the cannula. The constraining feature may be shaped to constrain displacement of the optical fiber to a particular range of motion. In an aspect, the particular range of motion is a plane. In an aspect, the constraining feature is a localized constriction permitting a higher amount of cross-lateral displacement and a relatively lower amount of lateral displacement.

In an aspect, the pivot feature is a crimp in the cannula. In an aspect, the pivot feature is an insert disposed in the cannula. In an aspect, the pivot feature is disposed at a location proximal of the cannula. In an aspect, the driver is disposed at a side of the optical fiber and arranged to displace the portion of the optical fiber in a direction orthogonal to the axis of the cannula.

In an aspect, the OCT probe may include a probe housing, the cannula extending from the probe housing and the driver being disposed in the probe housing. In an aspect, wherein the driver is spaced from the pivot feature along the optical fiber by a first distance, and wherein the distal end of the optical fiber is spaced from the pivot feature by a second distance greater than the first distance.

In another exemplary aspect, the present disclosure is directed to an OCT probe for imaging patient tissue. The OCT probe may include a cannula adapted to penetrate patient tissue and having a cannula axis, and may include a selectively displaceable light-carrying optical fiber disposed within the cannula and having a distal end. The optical fiber may be adapted to emit light from the distal end and out of the cannula. An actuation system may include a driver adapted to displace a portion of the optical fiber a first distance and to displace the distal end of the optical fiber a second distance greater than the first distance.

In an aspect, the actuation system includes a pivot feature that forms a fulcrum for the optical fiber. In an aspect, the driver is spaced from the pivot feature a first distance, and wherein the distal end of the optical fiber is spaced from the pivot feature a second distance, the second distance being greater than the first distance. In an aspect, the pivot feature is disposed between the driver and the distal end of the optical fiber.

In another exemplary aspect, the present disclosure is directed to a method of scanning with an OCT probe that includes emitting light from a distal end of an optical fiber in a cannula of the OCT probe, and actuating a driver to pivot the optical fiber about a pivot feature. The pivot feature may be disposed relative to the driver and relative to the distal end of the optical fiber to create a positive mechanical advantage that displaces the distal end of the optical fiber a distance greater than the actuation distance of the driver.

In an aspect, actuating a driver to pivot the optical fiber about a pivot feature includes actuating the driver in a direction orthogonal to an axis of the cannula. In an aspect, the pivot feature is one of a crimp in the cannula and an insert in the cannula. In an aspect, the pivot feature is disposed proximal of the cannula. In an aspect, the method also includes restricting lateral movement of the optical fiber with a constraining feature while actuating the driver to pivot the optical fiber about the pivot feature.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the exemplary embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to OCT probes, OCT systems, and methods that scan tissue to obtain an OCT image. The probe includes a light system including a lens and an optical fiber that directs light through the lens and captures reflected light that passes back through the lens. To obtain a scan of an area or a line, rather than merely a point, at least a portion of the light system moves relative to the tissue.

In an aspect described herein, the OCT probes, OCT systems, and methods disclosed herein utilize a pivoting technique to move an optical fiber within a long and narrow cannula to deflect light by laterally offsetting the light input to a lens, thereby causing the output beam to deflect angularly. The pivoting technique includes using the optical fiber as an extending lever arm to obtain a mechanical advantage. The movement of the light source relative to the tissue provides the scan, increasing the distance or area of the scanned tissue in order to create an image.

Figure 1:
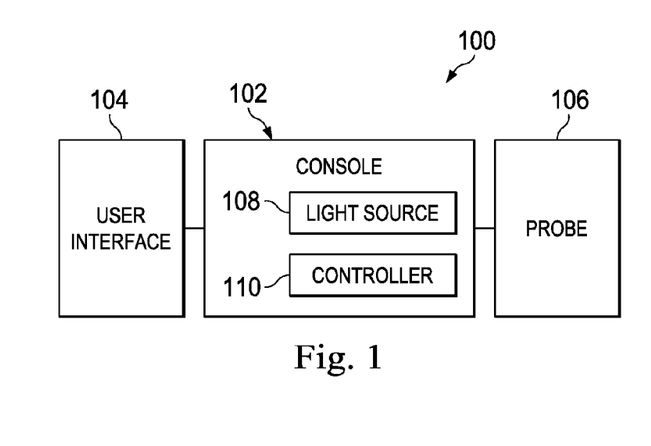
FIG. 1 is a block diagram of an exemplary OCT imaging system.

FIG. 1 shows an exemplary example of an OCT imaging system 100. The system 100 includes a console 102, a user interface 104, and an OCT probe 106. The console 102 includes an OCT engine including, among other elements, a light source 108 and a controller 110. In some instances, the light source 108 is configured to provide near-infrared light. In other implementations, radiation having other frequencies may be used. Any defined bandwidth of light frequencies may be used with OCT. For many ophthalmic applications, near-infrared may be used. For example, radiation bandwidth frequencies of 700 to 900 nm with a center wavelength of 800 nm may be used in some ophthalmic applications. In other instances, a radiation wavelength band of 1250-1450 with a center wavelength of 1350 nm may be used. Still further, a radiation wavelength band of 1400-1600 with a center wavelength of 1500 nm may be used. Further, while examples provided herein may be described in the context of ophthalmic procedures, the scope of the application is not so limited. Rather, the concepts presented herein may also be used in other applications. For example, the concepts may be used in other medical procedures. Still further, the concepts described herein may be used in any other suitable area. Particularly, the concepts described may be used in areas outside of the medical arts.

The light may be directed toward and reflected and captured from the target biological tissue through the OCT probe 106. In some embodiments, the light source 108 may include super-luminescent diodes, ultra-short pulsed lasers, or supercontinuum lasers that provide relative long wavelength light. The controller 110 may include a processor and memory that may include an executable program for operating the light source 108, the user interface 104, and the OCT probe 106, and for executing and performing functions and processes to carry out an OCT imaging procedure.

In some embodiments, the user interface 104 is carried on or forms a part of the console 102. The user interface 104 may be a display configured to present images to a user or a patient, and display tissue scanned by the probe 106 during an OCT imaging procedure. The user interface 104 also may include input devices or systems including, by way of non-limiting example, a keyboard, a mouse, a joystick, dials, and/or buttons, among other input devices.

The OCT probe 106 is sized and shaped to be handled by a user, such as a surgeon or other medical professional, and to protrude into a body of the patient. In the embodiment shown, the OCT probe 106 is in electrical and optical communication with the console 102 and configured to present light from the light source 108 onto patient tissue for the purpose of imaging the tissue.

Figure 2:
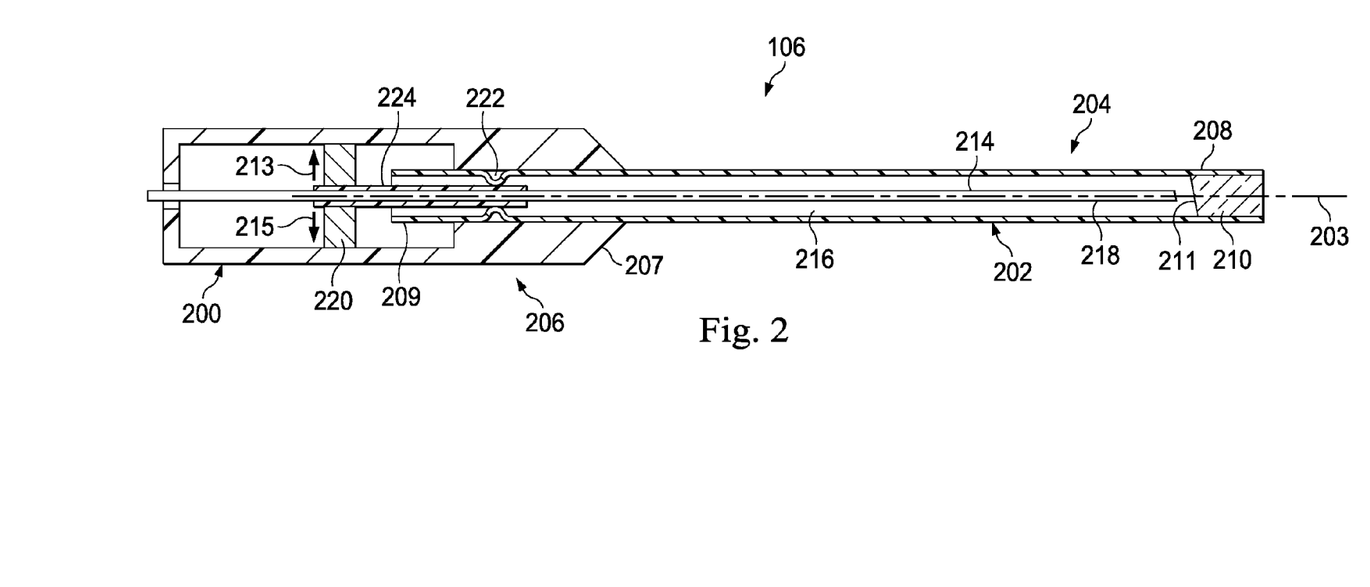
FIG. 2 is a cross-sectional view of an example OCT probe.
Figure 3:
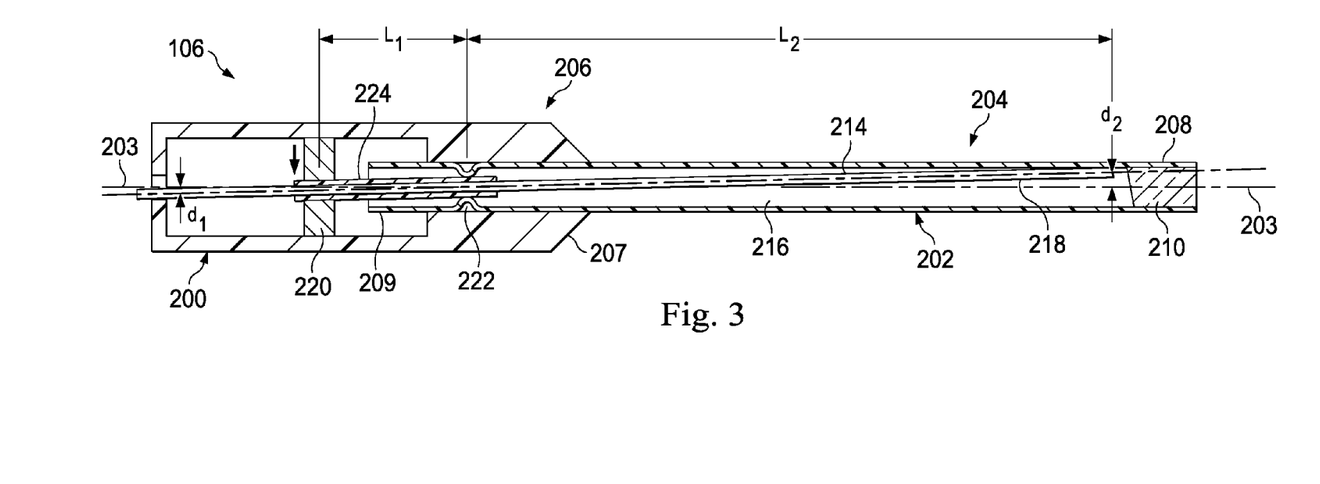
FIG. 3 is another cross-sectional view of the example OCT probe shown in FIG. 2.

FIGS. 2 and 3 show cross-sectional views of an exemplary OCT probe 106. As will be described in greater detail below, the OCT probe 106 includes a mechanism for actuation of an optical fiber carrying light from the light source 108 in a manner that moves the optical fiber relative to a lens. Light from the optical fiber transmits through the lens. An angular scan is produced by moving the position of the light beam laterally with respect to the lens.

Referring to both FIGS. 2 and 3, the OCT probe 106 includes a probe housing 200, a cannula 202, a lighting system 204, and an actuation system 206. In some implementations, the cannula may be formed form a metal, a polymer, a composite material, or any other suitable or desired material. The probe housing 200 is configured to be grasped and manipulated by a user, such as during an OCT procedure. A portion of the housing 200 may form a handle or grip and may house components of the OCT probe 106. The cannula 202 projects from a distal end 207 of the probe housing 200 and is configured and arranged to penetrate patient tissue in order to obtain an OCT image. The cannula 202 includes a distal end 208 and a proximal end 209. The proximal end 209 of the cannula 202 is disposed within and supported by the probe housing 200. In some embodiments, a lumen 216 of the cannula 202 receives a portion of the actuation system 206 and the lighting system 204 in the manner described below. In some instances, the cannula 202 may be sized to penetrate and be used within an eye and may be used to scan tissue of a patient. For example, in some instances, the cannula 202 may be utilized to scan eye tissue of a patient, such as retina tissue. The cannula 202 defines a central axis 203.

The lighting system 204 includes a lens 210 and an optical fiber 214. The lighting system 204 receives and transmits light from the light source 108. In some implementations, the lens 210 may be a gradient index (GRIN) lens having flat surfaces through which light from the optical fiber 214 may pass. In some implementations, the gradient index may be spherical, axial, or radial. In other instances, the lens 210 may be a spherical lens. In still other instances, other lens shapes may be used.

The optical fiber 214 is configured to transmit light from the light source 108 to the lens 210, and ultimately to the tissue under observation. In some instances, the optical fiber 214 may be a single optical fiber. In other instances, the optical fiber 214 may be a bundle of optical fibers. In some instances, the optical fiber 214 may be a continuous optical fiber extending from the light source 108 to distal end 218 of the optical fiber 214. In other instances, the optical fiber 214 may be formed from two or more optical fibers extending from the light source 108. Further, in still other implementations, the optical fiber 214 may receive light from the light source 108 from an optical fiber extending from the console 102 to the OTC probe 106.

In some instances, a proximal end (not shown) of the optical fiber 214 may be disposed adjacent the light source 108, while a distal end 218 may be disposed adjacent the lens 210 in a manner directing light through the lens 210. As shown in FIGS. 2 and 3, the optical fiber 214 is not directly connected to the lens 210, and the lens 210 is fixed in place relative to the cannula 202. Accordingly, the optical fiber 214 may move relative to the cannula 202 and the lens 210. The distal end 218 of the optical fiber 214 may be positioned a pre-determined distance from a proximal face 211 of the lens 210 to achieve prescribed optical working distance and focus spot size.

The actuation system 206 may be disposed primarily within the probe housing 200. In this example, the actuation system 206 includes a driver 220, a pivot feature 222, and a stiffening tube 224. The actuation system 206 is operable to move the optical fiber 214 of the lighting system 204 relative to the cannula 202 in order to provide either one or two dimensional directional scanning to create 2D or 3D images with the OCT imaging system 100.

The driver 220 may be a microelectrical mechanical systems (MEMS) micrometer, a linear motor, a piezoelectric motor, an electro-magnetic motor, a pneumatic piston, diaphragms, electrical solenoid, or other such element. The driver 220 is configured to impart a force on the optical fiber 214 to physically displace the optical fiber 214 in as the directions indicated by the arrows 213, 215 associated with the driver 220 in FIG. 2. Because of the arrangement described below and providing a positive mechanical advantage, the driver 220 may be selected to have a stroke distance that is less than a desired displacement distance of the distal end 218 of the optical fiber 214. In some embodiments, the driver 220 is electrically powered and is electrically connected to the console 102 by a power cable (not shown) extending from the OCT probe 106. In other embodiments, the driver 220 is disposed in the probe housing 200 and is configured to be self-contained on the driver 220. Accordingly, such embodiments may include a power source carried on the probe housing 200 that provides power to the driver 220 to physically displace the optical fiber 214 within the cannula 202. For example, the power source may be in the form of a one or more batteries or other power sources. In some embodiments, the driver 220 is configured to displace the portion the optical fiber 214 in a back and forth direction by applying force or loading on opposing sides of the optical fiber 214, to create a rocking effect about the pivot feature 222. In other embodiments, the driver 220 is configured to displace the portion the optical fiber 214 in only a single direction by applying force of loading on one side of the optical fiber 214 or in one direction. A biasing member (not shown), such as a spring, may act on the opposing side to create a rocking effect about the pivot feature 222.

In some instances, the pivot feature 222 may be a local constriction arranged to permit at least a portion of the lighting system 204 to pivot so that a portion of the lighting system 204 moves relative to the cannula 202. The pivot feature 222 may be formed of any structure providing a pivot point that enables a portion of the lighting system 204 to move so as to provide one or two dimensional directional scanning. In the exemplary embodiment shown, the pivot feature 222 is one or more fulcrums cooperating to allow the optical fiber 214 to pivot as a lever. The pivot feature 222 may be a first and second fulcrum. As shown in FIGS. 2 and 3, the pivot feature 22 may be formed as a result of a crimp in the cannula 202 on at least one side of the optical fiber 214. In other embodiments, the pivot feature 222 may be a component or element separate from the cannula 202, or that may be inserted into the cannula 202 in order to function as the fulcrum. In some embodiments, the pivot feature 222 is a protruding body disposed about the optical fiber 214, such as an O-ring or other body. In other embodiments, the pivot feature 222 is formed of a component disposed at the proximal end 209 of the cannula 202, and the optical fiber 214 extends therethrough. In yet other embodiments, the pivot feature 222 may be in the form of an opening through one or more components of the OTC probe 106. For example, the pivot feature 222 may be formed as an opening in the probe housing 200. Yet other pivot features 222 are contemplated.

The stiffening tube 224 includes a hollow channel through which the optical fiber 214 extends. The stiffening tube 224 may be formed from metal, a polymer, a composite material, or any other suitable or desired material. The stiffening tube 224 may be formed of a rigid material in order to provide rigidity to the optical fiber 214 and, at the same time, provide a rigid interface that cooperates with the pivot feature 222. Because of the rigid interface, the stiffening tube 224 may pivot about the fulcrum formed by the pivot feature 222 with minimal resistance, and therefore in response to a minimal force. This may help the driver 220 pivot the optical fiber 214 in an efficient manner with a minimal level of loading. In the embodiment shown, the stiffening tube 224 extends from a location just proximal of the driver 220 to a location just distal of the pivot feature 222. However, in other embodiments, the stiffening tube 224 extends the length of the optical fiber 214 from adjacent the distal end 218 to a location adjacent or just proximal the driver 220. The stiffening tube 224 may be disposed along or may extend along other lengths of the optical fiber 214.

The actuation system 206 is configured to pivot the optical fiber 214 in a manner that causes the distal end 218 of the optical fiber to displace relative to the cannula 202, and thereby move the optical fiber 214 in at least a single plane to perform a scan. Scanning allows light to be taken over an area of the tissue being evaluated, rather than a specific spot or point on the tissue. The scan is then converted into a 2D or 3D image by the OCT system 100 that may be evaluated by the health care provider.

The embodiment shown in FIGS. 2 and 3 is arranged so that the actuation system 206 can produce movement of the optical fiber 214 for the scan with a low amount of input energy and with a minimal amount of driver displacement or driver stroke, enabling smaller cost-efficient drivers to be utilized. This is possible due to the actuation system 206 being disposed and arranged on the optical fiber 214 to provide a positive mechanical advantage. Here, the pivot feature 222 is disposed between the driver 220 and the distal end 218 of optical fiber 214, dividing the optical fiber 214 into a length L1 referenced herein as an actuation arm length, and a length L2 referenced herein as a fiber arm length, as shown in FIG. 3. For a simple lever, the mechanical advantage MA may be determined using the equation:

MA=fiber arm length L2/actuation arm length L1

In the example shown, since the fiber arm length L2 is greater than the actuation arm length L1, the actuation system 206 is configured to provide a positive mechanical advantage, in that mechanical advantage MA is greater than the value 1. The practical effect is that a small displacement of the optical fiber 214 at the location of the driver 220 results in a larger displacement at the distal end 218 of the optical fiber 214. By using an arrangement that provides a positive mechanical advantage MA, a minimal input may be used to provide a suitable displacement to carry out a scan procedure. In some embodiments, the actuation arm length L1 is within a range of about 2 mm to 12 mm, and the fiber arm length L2 is a range of about 4 mm to 35 mm. Thus, in some instances, a mechanical advantage in the range of 2 to 12.5 may be provided. In some embodiments, the actuation arm length L1 is about 8 mm, and the fiber arm length L2 is about 25 mm. This provides a mechanical advantage MA in the range of about 3:1. However, in some embodiments, the actuation system 206 may be arranged to provide any positive mechanical advantage. Because of the mechanical advantage MA, displacement of the distal end 218 of the optical fiber 214 may be greater than the stroke at the driver 220, enabling relatively small drivers to be employed to move the optical fiber.

For the example OCT probe 106 shown in FIGS. 2 and 3, the pivot feature 222 is disposed between the lens 210 and the driver 220, with the driver 220 proximal of the pivot feature 222. However, other arrangements are contemplated that provide a mechanical advantage. In some implementations, the driver 220 is disposed distal of the pivot feature 222, between the pivot feature 222 and the distal end 218. In such instances, the pivot feature 222 may still be arranged to provide a positive mechanical advantage. Other arrangements are also contemplated.

FIG. 3 shows the OCT probe 106 with the optical fiber 214 deflected from the central axis 203 of the cannula 202. The optical fiber 214 is deflected about the fulcrum formed by the pivot feature 222. As can be seen, a small deflection d1 from the central axis at the driver 220 results in a larger deflection d2 at the distal end 218 of the optical fiber 214. Because a small deflection or stroke at the driver 220 may result in a larger scan or displacement of the distal end 118 of the optical fiber 214, the driver 220 may be selected with a relatively small stroke or to displace the optical fiber 214 only a short distance, while still effecting the larger desired displacement of the distal end 218 of the optical fiber 214.

Figure 4:
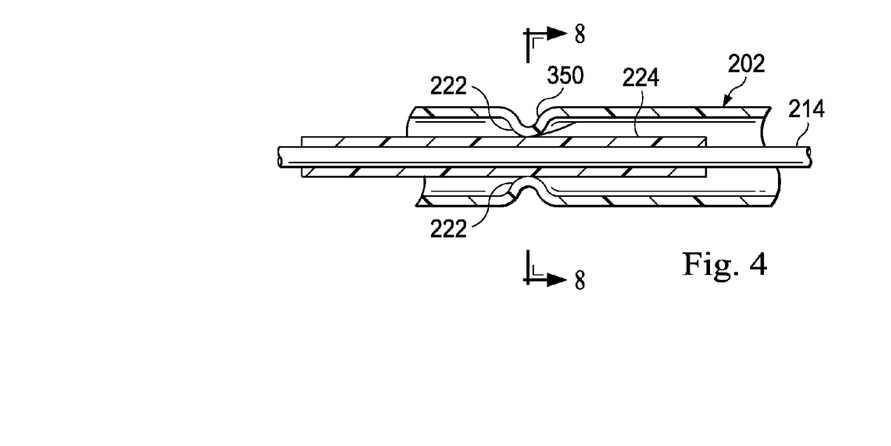
FIG. 4 is a detail cross-sectional view of a portion of the example OCT probe shown in FIG. 2 illustrating a pivot feature thereof.
Figure 8:
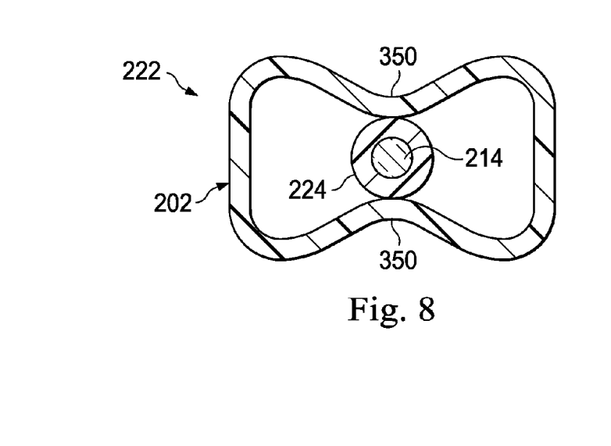
FIG. 8 is a cross-sectional view of an example pivot feature taken along 8-8 in FIG. 4.

FIG. 4 shows a portion of the OCT probe 106 with an enlarged pivot feature 222, shown in cooperation with the optical fiber 214 and the stiffening tube 224. In this example the pivot feature 222 is shown as a crimp 350 formed in a cannula 202 of the probe 106. Here, the crimp 350 on opposing sides of the cannula allows the optical fiber 214 and the stiffening tube 224 to be maintained along a central axis through the cannula, providing a high range of pivot capability. A cross-sectional view of the crimp 350 as the pivot feature 222 is shown in FIG. 8, taken along 8-8 in FIG. 4. As can be seen, the crimp 350 is a local constriction in the cannula 202 that restricts or limits lateral displacement of the optical fiber 214 at the fulcrum, allowing the optical fiber 214 to pivot about the crimp 350.

Figure 5:
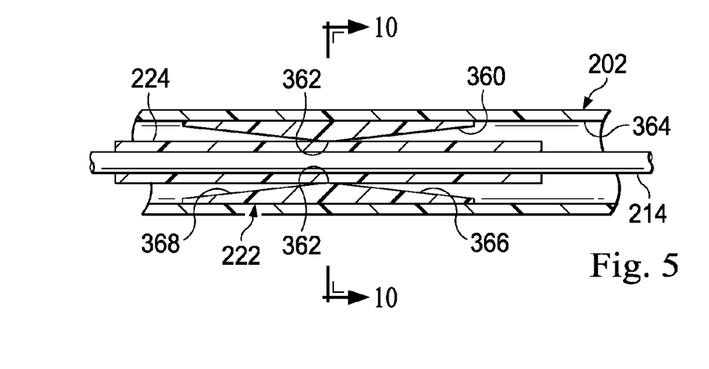
FIG. 5 is a cross-sectional view of a portion of another example OCT probe illustrating a pivot feature thereof.
Figure 10:
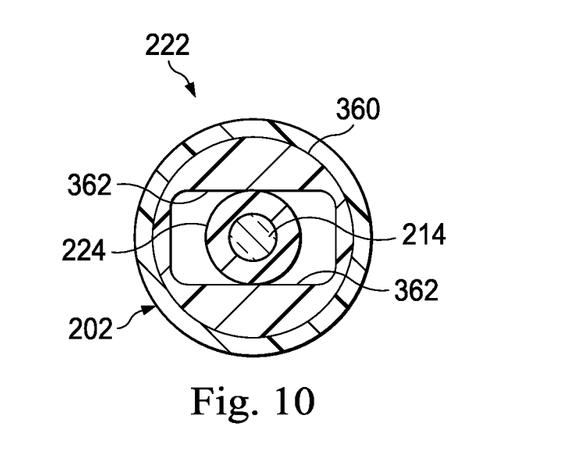
FIG. 10 is a cross-sectional view of an example pivot feature taken along 10-10 in FIG. 5.

FIG. 5 shows a portion of the OCT probe 206 with an alternative pivot feature 222, shown as an insert 360 in the cannula 202. The insert 360 is arranged to fit into the cannula 202 and may be bonded or otherwise secured in place. The insert 360 includes a peak 362 that acts as a fulcrum in the manner described above. Here, the insert 360 is shown in cross-section and has a circular exterior cross-sectional shape configured to match or otherwise conform to an inner cross-sectional shape a lumen 364 of the cannula 202, and includes tapered inner walls 366, 368 that converge to form the peak 362. The peak 362 defines a pivot location for the optical fiber 214 and the stiffening tube 224. A cross-sectional view of the insert 360 as the pivot feature 222 is shown in FIG. 10, taking along 10-10 in FIG. 5. As can be seen, the insert 360 in the cannula 202 forms a constriction that restricts or limits movement at the fulcrum in at least one direction, allowing the optical fiber 214 to pivot about the insert 360.

Figure 6:
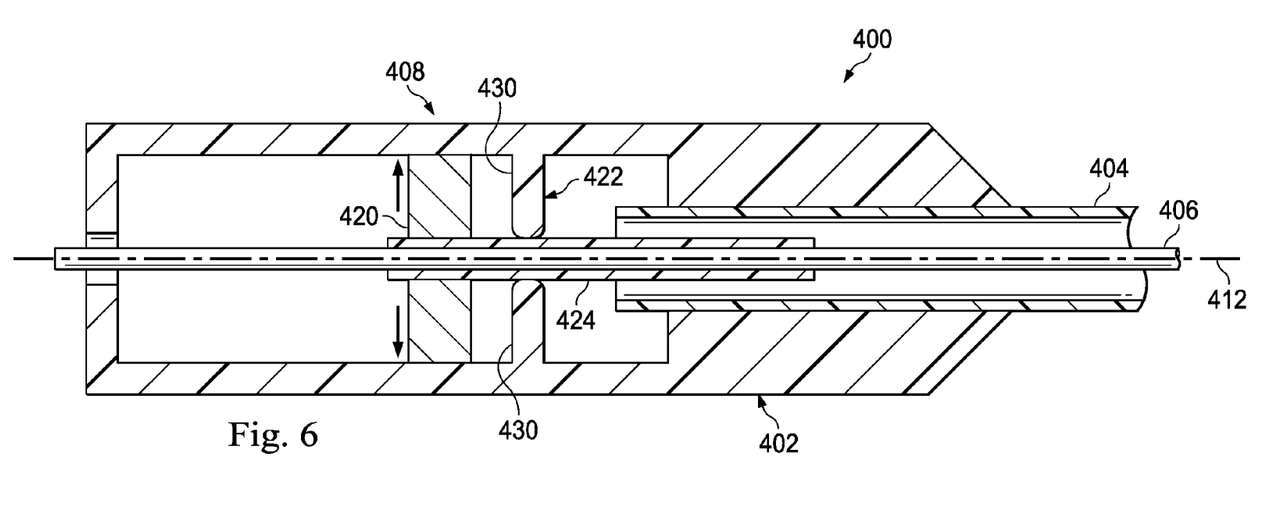
FIG. 6 is a cross-sectional view of a portion of another example OCT probe showing a pivot feature thereof.

FIG. 6 shows a detail view of an alternative example OCT probe 400. The OCT probe 400 includes a probe housing 402, a cannula 404, an optical fiber 406 forming a part of a light source, such as in a manner similar to that described above. The OCT probe 400 may also include an actuation system 408 and may otherwise be similar to the OCT probe 106 describe above except where otherwise described.

The actuation system 408 may include a driver 420, a pivot feature 422, and a stiffening tube 424. Here, the pivot feature 422 is separate and independent of the cannula 404. The pivot feature 422 includes pivot protrusions 430 that project from a portion of the probe housing 402. These pivot protrusions 430 forms a narrow passage through which the optical fiber 406 passes and operates in the manner similar to that described above. Thus, these pivot protrusions also act as local constrictions or fulcrums about which the optical fiber 406 can pivot. As can be seen in FIG. 6, the pivot protrusions 430 extend to maintain the optical fiber 406 in a central position aligned with a central axis 412 of the cannula 202. The driver 420 operates from a location proximal of the pivot feature 422 and is arranged to provide a positive mechanical advantage.

Figure 7:
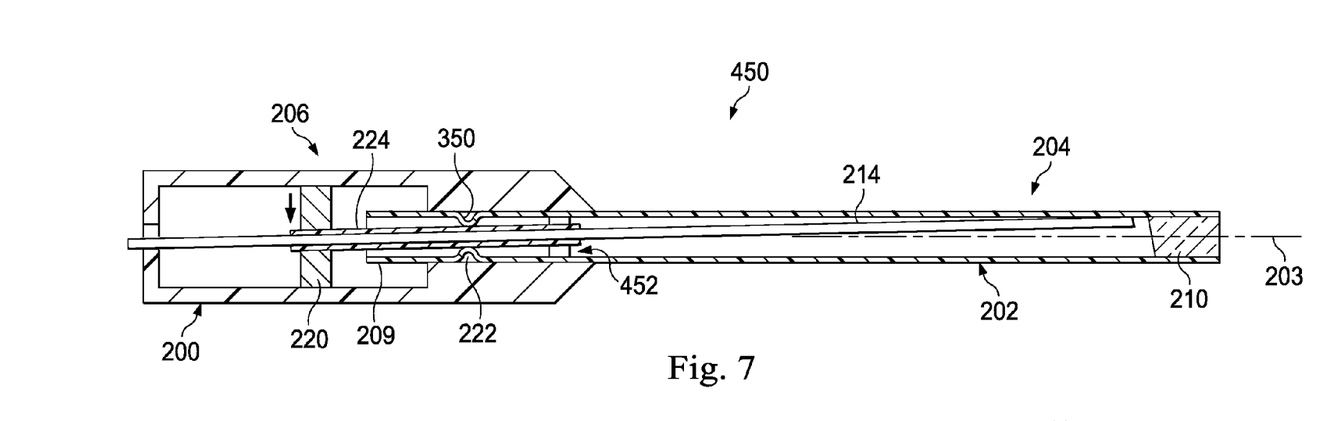
FIG. 7 is a cross-sectional view of a of another example OCT probe.

FIG. 7 shows another example OCT probe 450. The OCT probe 450 includes the lighting system 204 and the actuation system 206 described above. Here, however, the stiffening tube 224 is shown as extending along a longer portion of the optical fiber 214 than the stiffening tube 224 shown in FIGS. 2 and 3. The OCT probe 450 also includes a constraining feature 452 that cooperates with the pivot feature 222 to constrain the motion of the optical fiber 214 and stiffening tube 224 within a plane.

Figure 9:
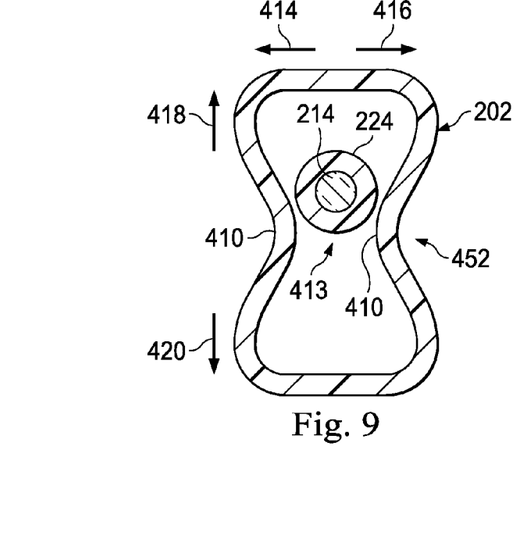
FIG. 9 is a cross-sectional view of an example constraining feature.

FIGS. 8 and 9 respectively show the pivot feature 222 and the constraining feature 452 that cooperate to constrain the motion of the optical fiber 214 to a particular range of motion, such as motion within a plane. FIG. 8 shows the pivot feature 222 as a crimp 350 in the cannula 202. Examples of crimps forming pivot features are shown in FIGS. 4 and 7. As can be seen in FIG. 8, the optical fiber 214, with or without the stiffening tube 224, passes through the opening at the crimp 350 in a manner that allows the sides of the crimp 350 to act as fulcrums.

FIG. 9 is a cross-sectional view of the constraining feature 452 shown in FIG. 7. In some instances, the constraining feature 452 may be formed as a crimp 410 in the cannula 202. In some instances, the crimp 410 may be formed to be orthogonal to the crimp 350 so that the constraining feature 452 constrains the motion of the optical fiber 214 through a single plane while the fiber pivots at the crimp 350. The orthogonal relationship between crimp 410 and crimp 350 is shown in FIGS. 8 and 9, as these two cross-sections represent the orientation of these features relative to each other along the cannula 202.

A constriction 413 formed by the crimp 410 through which the optical fiber 214 and, in some instances, stiffening tube 224 may be sized to constrain the motion of the optical fiber 214 and the stiffening tube 224 in lateral directions such as those indicated by arrows 414, 416. While constraining movement of the optical fiber 214 in lateral directions 414, 416, the configuration of the constriction 413 may also allow motion in a cross-lateral, or orthogonal, direction indicated by arrows 418, 420. Accordingly spurious motions outside the desired envelope of motion may be reduced, minimized, and/or eliminated. In some implementations, the constraining feature 452 may be situated at a location distal of the pivot feature 222, as shown in FIG. 7.

Figure 11:
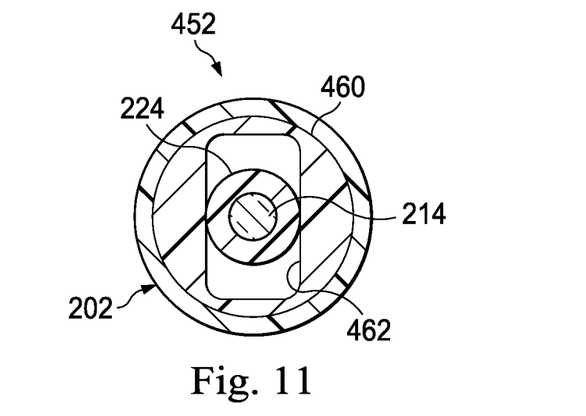
FIG. 11 is a cross-sectional view of another example constraining feature.

FIGS. 10 and 11 respectively show the pivot feature 222 and the constraining feature 452 that cooperate to constrain the motion of the optical fiber 214 a particular range of motion, such as constraining motion to a plane. As described above, the pivot feature 222 in FIG. 10 is the insert 360 insertable in the cannula 202, as shown in FIG. 5. As can be seen, the optical fiber 214, with or without the stiffening tube 224, passes through the opening at the pivot feature 222 in a manner that allows the peaks 362 of the insert 360 to act as fulcrums.

In this embodiment, the constraining feature 452 is also an insert 460 that may be disposed in the cannula 202 at a location distal of the pivot feature 222 and may provide a constriction orthogonal to the constriction of the pivot feature 222. The size of opening in the constraining feature 452 may be sufficiently sized to constrain the motion of the optical fiber 214 and the stiffening tube 224 in a lateral direction, while allowing motion in a cross-lateral, or orthogonal, direction. Here, the opening of the constraining feature 462 is oriented orthogonal to the opening of the insert 360 forming the pivot feature 222. The constraining feature 462 serves to constrain the motion of the optical fiber 214 within a plane defined by the narrow opening 462 formed by the constraining feature 360. The size of the opening 462 in the constraining feature 360 may be selected to be long enough to sufficiently constrain the motion of the optical fiber 214 in unwanted directions. In some embodiments, both the pivot feature 222 and the constraining feature 452 are formed of the same insert. That is, in some implementations, two identical inserts may be used for both insert 360 and insert 460, one being rotated 90° relative to the other. In still other implementations, the pivot feature 222 and the constraining feature 452 may be formed in a single insert disposed within the cannula 202.

While the examples above are shown as having the lens 210 fixed in place relative to the cannula 202, other embodiments have the lens 210 in a fixed spatial relationship with the distal end 218 of the optical fiber 214 (e.g., the optical fiber 214 and lens 210 are coupled together). This optical arrangement forms the basis of an A-scan OCT in which the information is gathered at the single focal point. If the optical fiber 214 and lens 210 are then physically moved, a scan can be produced. Yet other embodiments are contemplated.

In operation, a user controls the OCT probe 106 at the console 102 and then orients the OCT probe 106 at a location adjacent tissue to be evaluated. With the OCT probe 106 at its desired location, the OCT probe 106 is activated to begin a scanning procedure. To do this, the actuation system 206 operates to physically displace the optical fiber 214 relative to the cannula 202 (and in some embodiments the lens) in a back and forth motion. The driver 220 operates to displace the optical fiber 214 in a direction substantially orthogonal to the axial direction of the optical fiber 214, causing the optical fiber 214 to pivot about the pivot feature 222, which may be formed of local constrictions in the manner described herein. The OCT probe 400 may be operated in a similar manner.

The OCT probe 106 is arranged so that a physical displacement by the driver 220 of a first amount results in a physical displacement of the distal end 218 of the optical fiber 214 by a second amount greater than the first amount. Accordingly, the OCT probe 106 is arranged to provide a positive mechanical advantage.

Embodiments having both a pivot feature and a constraining feature may be arranged so that the fiber displacement occurs substantially within a plane defined by the constraining features. In some embodiments, the constraining feature is oriented orthogonally to the pivot feature.

In some aspects, by creating a fulcrum by means of several possible embodiments described, and taking advantage of the multiplication of stroke from an actuator, present disclosure solves a problem of the limitation of availability of inexpensive actuators with sufficient stroke to provide adequate actuation.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An OCT probe for imaging patient tissue, comprising:
a cannula having a cannula axis;
a selectively displaceable light-carrying optical fiber disposed within the cannula and having a distal end, the optical fiber being adapted to emit light from the distal end;
an actuation system arranged to displace the optical fiber within the cannula, the actuation system comprising:
a driver actuatable to displace a portion of the optical fiber, the driver acting in an angled direction relative to the cannula axis; and
a pivot feature operably engaged with the optical fiber, the optical fiber pivotable about the pivot feature in response to a displacement of the portion of the optical fiber by the driver; and a stiffening tube disposed about the optical fiber and separating the optical fiber and the pivot feature, the stiffening tube directly engaging the pivot feature in a pivot relationship, wherein the driver is spaced from the pivot feature along the optical fiber by a first distance, and wherein the distal end of the optical fiber is spaced from the pivot feature by a second distance greater than the first distance.

2. The OCT probe of claim 1, wherein the stiffening tube extends from at least the pivot feature to the driver.

3. The OCT probe of claim 1, further comprising a constraining feature disposed in the cannula, the constraining feature being shaped to constrain displacement of the optical fiber to a particular range of motion.

4. The OCT probe of claim 3, wherein the particular range of motion is within a plane.

5. The OCT probe of claim 1, wherein the constraining feature is a localized constriction permitting a higher amount of cross-lateral displacement and a relatively lower amount of lateral displacement.

6. The OCT probe of claim 1, wherein the pivot feature is a crimp in the cannula.

7. The OCT probe of claim 1, wherein the pivot feature is an insert disposed in the cannula.

8. The OCT probe of claim 1, wherein the pivot feature is disposed at a location proximal of the cannula.

9. The OCT probe of claim 1, wherein the driver is disposed at a side of the optical fiber and arranged to displace the portion of the optical fiber in a direction orthogonal to the axis of the cannula.

10. The OCT probe of claim 1, further comprising:
a probe housing, the cannula extending from the probe housing and the driver being disposed in the probe housing.

11. An OCT probe for imaging patient tissue, comprising:
a cannula adapted to penetrate patient tissue and having a cannula axis;
a selectively displaceable light-carrying optical fiber disposed within the cannula and having a distal end, the optical fiber adapted to emit light from the distal end; and
an actuation system comprising a driver adapted to displace a portion of a the optical fiber a first distance and to displace the distal end of the optical fiber a second distance greater than the first distance, wherein the actuation system comprises a pivot feature that forms a fulcrum for the optical fiber and wherein the pivot feature is disposed between the driver and the distal end of the optical fiber,
wherein the driver is spaced from the pivot feature a first distance, and wherein the distal end of the optical fiber is spaced from the pivot feature a second distance, the second distance being greater than the first distance.

12. The OCT probe of claim 11, further comprising a lens disposed in the cannula distal of the optical fiber and moveable with the optical fiber.

* * * * *